US00PP14471P39

(12) United States Plant Patent
Pieters

(10) Patent No.: US PP14,471 P3
(45) Date of Patent: Jan. 20, 2004

(54) CHRYSANTHEMUM PLANT NAMED 'GEDI TWO COR'

(50) Latin Name: *Chrysanthemum morifolium*
Varietal Denomination: Gedi Two Cor

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 10/137,812

(22) Filed: May 1, 2002

(65) Prior Publication Data

US 2003/0208811 P1 Nov. 6, 2003

(51) Int. Cl.[7] ..... A01H 5/00
(52) U.S. Cl. ..... Plt./288
(58) Field of Search ..... Plt./288, 287

(56) References Cited

U.S. PATENT DOCUMENTS

PP10,215 P 1/1998 Pieters ..... Plt./289
PP12,259 P2 12/2001 Pieters ..... Plt./294

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant cultivar is disclosed, characterized by a decorative-type inflorescence, consistent flowering response to short days, blooming consistently after 46 days of short day length, free branching habit, yellow colored inflorescence at first opening which fades to white, with the yellow color remaining in the center at full bloom and with the inflorescence becoming completely white at fading, a very uniform round growth habit, and a large quantity of blooms per flowering branch.

2 Drawing Sheets

Latin name of the genus and species: The present invention relates to a new and distinct cultivar of Chrysanthemum plant, botanically known as *Chrysanthemum morifolium.*

Variety denomination: The new and distinct Chrysanthemum plant is hereinafter referred to by the cultivar name 'Gedi Two Cor.'

BACKGROUND OF THE INVENTION

The new cultivar is a product of hybridization of a female parent Chrysanthemum plant variety 'Gedi One Ter' (U.S. Plant Pat. No. 13,885) and a male parent Chrysanthemum plant variety 'Dark Veria' (U.S. Plant Pat. No. 10,215). The new cultivar was discovered and selected by the inventor in September 1995.

Asexual reproduction of the new cultivar by apical tip cutting and meristem tissue culture was performed in Oxnard, Calif. and has shown that the unique features of this cultivar are stable and reproduced true to type on successive generations.

SUMMARY OF THE INVENTION

The cultivar 'Gedi Two Cor' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi Two Cor.' These characteristics in combination distinguish 'Gedi Two Cor' as a new and distinct Chrysanthemum cultivar:

1. Decorative-type inflorescence,
2. Consistent flowering response to short days, blooming consistently after 46 days of short day length, 3. Free branching habit,
4. Yellow colored inflorescence at first opening which fades to white, with the center becoming about 18D at full bloom and with the inflorescence becoming completely white at fading,
5. Very uniform round growth habit, and
6. Large quantity of blooms per flowering branch.

Plants of the new cultivar are similar to plants of the female parent variety, 'Gedi One Ter' in most horticultural characteristics, however plants of the new cultivar have fewer ray florets and a smaller diameter inflorescence than plants of the female parent variety. Plants of the new variety also naturally bloom later than plants of the female parent variety.

Plants of the new cultivar are similar to plants of the male parent variety, 'Dark Veria' in most horticultural characteristics, however plants of the new cultivar have ray florets of a different color and are taller than plants of the male parent variety. Plants of the new cultivar also naturally bloom earlier than plants of the male parent variety.

In comparison to the commercially available variety 'Gedi Wo' (U.S. Plant Pat. No. 12,259), 'Gedi Two Cor' blooms one to two weeks earlier naturally and has a decorative type inflorescence, more ray florets per inflorescence, and more inflorescences per flowering branch.

BRIEF DESCRIPTION OF THE PHOTOGRAPHS

DETAILED BOTANICAL DESCRIPTION

Figure 1:
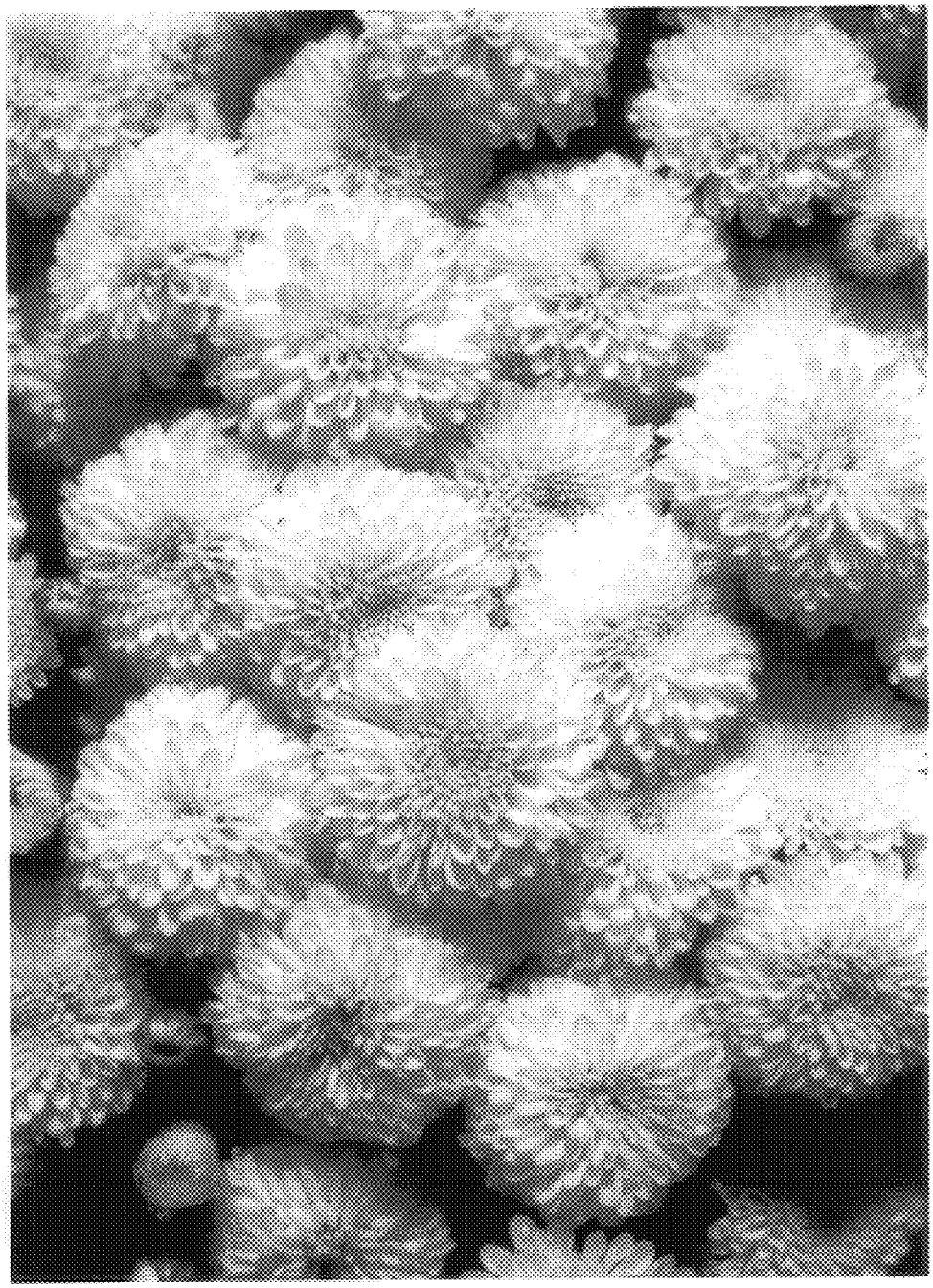
FIG. 1 shows a close up view of the flowers and buds of the new cultivar 'Gedi Two Cor.' One cutting was used in the pot.
Figure 2:
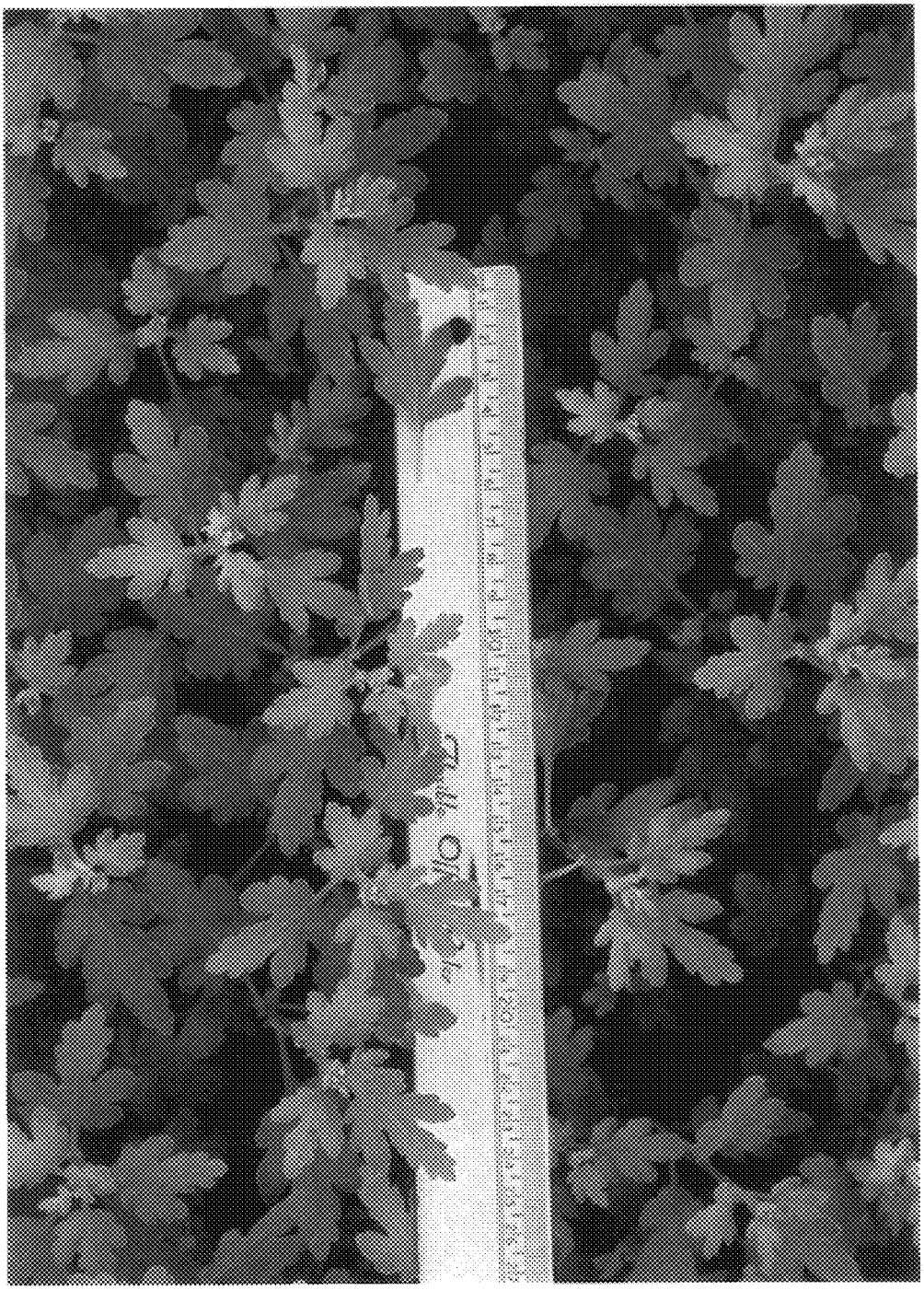
FIG. 2 shows the foliage of the new cultivar 'Gedi Two Cor.'

In the following description, color references are made to The Royal Horticultural Society Colour Chart except where general terms of ordinary dictionary significance are used. The following observations and measurements describe plants grown in Oxnard, Calif. during the month of December and January. The age of the observed plants is 88 days from a rooted cutting. The growing temperature ranged from 55° to 68° F. at night to 60° to 75° F. during the day. Measurements and numerical values represent averages of typical flowering types.

Botanical classification: *Chrysanthemum morifolium* cultivar 'Gedi Two Cor'.
Commercial classification: Garden-type Chrysanthemum.
Parentage: Hybridization of a female parent Chrysanthemum plant variety, 'Gedi One Ter' (U.S. Plant Pat. No. 13,885), and a male parent Chrysanthemum plant variety 'Dark Veria' (U.S. Plant Pat. No. 10,215).

PROPAGATION

Time to rooting: 7 to 14 days at approximately 21° C.
Root description: Fine, fibrous.

PLANT

Growth habit: Mounding herbaceous perennial.
Height: Approximately 20.5 cm.
Spread: Approximately 23 cm.
Growth rate: Moderate.
Branching characteristics: Free Branching.
Length of lateral branches: Approximately 17 cm.
Number of leaves per lateral branch: Approximately 11.

FOLIAGE

Leaf:
- *Arrangement.*—Alternate.
- *Average length.*—Approximately 5.6 cm.
- *Average width.*—Approximately 4.6 cm.
- *Shape of blade.*—Oval.
- *Apex.*—Cuspidate.
- *Base.*—Oblique.
- *Attachment.*—Stalked.
- *Margin.*—Palmately lobed.
- *Texture of top suraface.*—Lightly pubescent.
- *Texture of bottom surface.*—Lightly pubescent.
- *Color.*—Young foliage upper side: Near 137B. Young foliage under side: Near 138B. Mature foliage upper side: Near 137A. Mature foliage under side. Near 138B. Venation upper side. Near 138C. Venation under side: Near 139D.
- *Venation type.*—Palmately net.

Petiole:
- *Average length.*—Approximately 2.4 cm.
- *Color.*—Near 137A.
- *Diameter.*—Approximately 0.2 cm.

BLOOM

Inflorescence:
- *Flowering habit.*—Induced by darkness period greater than 13.5 hours, approximately 46 days of appropriate day length required to induce and develop blooms.
- *Inflorescence form.*—Decorative.
- *Natural flowering season.*—Approximately the middle two weeks of September.
- *Number of inflorescences per lateral branch.*—Approximately 23.
- *Inflorescence diameter.*—Approximately 2.8 cm.
- *Inflorescence depth.*—Approximately 1.2 cm.
- *Inflorescence longevity on plant.*—Approximately 24 days.
- *Persistence.*—Persistent.

Ray florets:
- *Appearance.*—Matte.
- *Texture.*—Smooth.
- *Average number per flower.*—168.
- *Shape.*—Obovate.
- *Aspect.*—*Flat.*
- *Margin.*—Entire.
- *Apex.*—Retuse.
- *Length.*—Approximately 1.4 cm.
- *Width.*—Approximately 0.6 cm.
- *Color.*—Upper surface at first opening: Near 7B. Upper surface at maturity: Near 155A. Upper surface at fading: Near 155A. Under surface at first opening: Near 8A. Under surface at maturity: Near 155A. Under surface at fading: Near 155A.

Disc florets:
- *Appearance.*—Shiny.
- *Texture.*—Smooth.
- *Average number per flower.*—Approximately 3.
- *Shape.*—Cylindric.
- *Apex.*—Obtuse.
- *Average length.*—Approximately 0.4 cm.
- *Average width.*—Approximately 0.1 cm.
- *Color.*—At first opening: Near 154C. At maturity: Near 3A. At fading: Near 7A.

Peduncle:
- *Length.*—At terminal end (shortest): Approximately 2 cm. At lateral end (longest): Approximately 3 cm.

*Angle to stem.*—Acute.
*Strength.*—Moderate.
*Color.*—Near 138B.
*Habit.*—Upright.
*Diameter.*—Approximately 0.2 cm.
*Surface texture.*—Lightly pubescent.

Inflorescence bud:
- *Length.*—Approximately 0.6 cm.
- *Diameter.*—Approximately 0.8 cm.
- *Form.*—Globular.
- *Color (as ray florets first emerge).*—Near 7B.

Involucral bracts (phyllaries):
- *Appearance.*—Matte.
- *Texture.*—Lightly pubescent.
- *Number.*—Approximately 29.
- *Shape.*—Ovate.
- *Margin.*—Entire.
- *Apex.*—Subacute.
- *Length.*—Approximately 0.6 cm.
- *Width.*—Approximately 0.4 cm.
- *Color.*—Upper side: Near 144A. Under side: Near 144A.

REPRODUCTIVE ORGANS

Ray florets:
- *Number of pistils per flower.*—1.
- *Stigma shape.*—2 branched.
- *Stigma color.*—Near 3A.
- *Style color.*—Near 154B.

*Style length.*—Approximately 0.5 cm.
*Stamens.*—Absent.

Disc florets:
*Number of pistils per flower.*—1.
*Stigma shape.*—Two-branched.
*Stigma color.*—Near 6A.
*Style length.*—Approximately 0.4 cm.
*Style color.*—Near 154D.
*Number of stamens per flower.*—5.
*Anther shape.*—Tubular.
*Anther color.*—Near 13A.
*Pollen.*—No pollen detected.

OTHER CHARACTERISTICS

Seed production: Commercially, this plant is not used or observed in a stage wherein seeds would be produced. Therefore, seed production has not been observed.

Disease resistance: Neither resistance nor susceptibility to diseases and pests has been observed in this cultivar.

Heat and cold resistance: Plants with flowers are hardy to low temperatures about −2° C. Non flowering plants are hardy in the approximate range of 3° C. to −6° C., depending upon duration of cold and amount of moisture in the soil. With adequate water plants are hardy to a high temperature of 49° C.

What is claimed is:

1. A new and distinct cultivar of Chrysanthemum plant named 'Gedi Two Cor' as herein illustrated and described.

* * * * *